(12) United States Patent
Kadereit et al.

(10) Patent No.: US 9,040,544 B2
(45) Date of Patent: May 26, 2015

(54) 2,5-SUBSTITUTED OXAZOLOPYRIMIDINE DERIVATIVES

(75) Inventors: Dieter Kadereit, Frankfurt am Main (DE); Matthias Schaefer, Frankfurt am Main (DE); Stephanie Hachtel, Frankfurt am Main (DE); Axel Dietrich, Frankfurt am Main (DE); Thomas Huebschle, Frankfurt am Main (DE); Katrin Hiss, Frankfurt am Main (DE)

(73) Assignee: Sanofi, Paris (FR)

( * ) Notice: Subject to any disclaimer, the term of this patent is extended or adjusted under 35 U.S.C. 154(b) by 67 days.

(21) Appl. No.: 13/521,825

(22) PCT Filed: Jan. 14, 2011

(86) PCT No.: PCT/EP2011/050303
§ 371 (c)(1),
(2), (4) Date: Nov. 15, 2012

(87) PCT Pub. No.: WO2011/086081
PCT Pub. Date: Jul. 21, 2011

(65) Prior Publication Data
US 2013/0072501 A1    Mar. 21, 2013

(30) Foreign Application Priority Data
Jan. 14, 2010   (EP) .................................. 10305044

(51) Int. Cl.
| | | |
|---|---|---|
| *A01N 43/90* | (2006.01) | |
| *A61K 31/519* | (2006.01) | |
| *C07D 239/00* | (2006.01) | |
| *C07D 471/00* | (2006.01) | |
| *C07D 487/00* | (2006.01) | |
| *C07D 491/00* | (2006.01) | |
| *C07D 498/04* | (2006.01) | |
| *C07D 498/22* | (2006.01) | |

(52) U.S. Cl.
CPC ............ *C07D 498/04* (2013.01); *C07D 498/22* (2013.01); *A61K 31/519* (2013.01)

(58) Field of Classification Search
None
See application file for complete search history.

(56) References Cited

U.S. PATENT DOCUMENTS

| 8,748,436 B2 | 6/2014 | Kadereit et al. |
| 2013/0072502 A1 | 3/2013 | Kadereit et al. |
| 2013/0079358 A1 | 3/2013 | Kadereit et al. |
| 2013/0137685 A1 | 5/2013 | Kadereit et al. |
| 2013/0158051 A1 | 6/2013 | Kadereit et al. |

FOREIGN PATENT DOCUMENTS

| WO | 2004096813 | 11/2004 |
| WO | 2005000833 | 1/2005 |
| WO | 2007061458 | 5/2007 |
| WO | 2007109334 | 9/2007 |
| WO | 2009013545 | 1/2009 |
| WO | 2009131926 | 10/2009 |
| WO | 2009154775 | 12/2009 |
| WO | 2010006704 | 1/2010 |

OTHER PUBLICATIONS

Boarland, et. al., Journal of the Chemical Society (1952) 4942-5.*
Anderson, The Process of Structure-Based Drug Design, Chem. Biol., 10:787-797, 2003.
Holschbach et al., Synthesis and Evaluation of 7-Amino-2-(2(3)-Furyl)-5-Phenylethylamino-Oxazolo[5,4-d] Pyrimidines as Potential A2A Adenosine Receptor Antagonists for Positron Emission Tomogrphy (PET), Eur. J. Med. Chem., 41:7-15, 2006.
International Search Report as issued in PCT/EP2011/050303, mailed on Feb. 16, 2011.
Johnson et al., Researches on Pyrimidines. LXXXVII. Alkylation of 5-Amino-Uracil, J. Am. Chem. Soc., 41 (5):782-789, 1919.
Johnson, CXXVI. Researches on Pyrimidines: 2-Ethyl-Mercapto-5-Amino-6-oxypyrimidine, J. Am. Chem. Soc., 34:191-204, 1905.
Mitsunobu, The Use of Diethyl Azodicarboxylate and Triphenylphosphine in Synthesis and Transformation of Natural Products, Synthesis, pp. 1-28, 1981.
Thiel, Structure-aided drug design's next generation, Nat. Biotechnol. 22(5):513-519, 2004.
Whittaker, A New Synthesis and the Chemical Properties of 5-Aminopyrimidine, J. Chem. Soc., pp. 1565-1570, 1951.

* cited by examiner

Primary Examiner — Jeffrey H Murray

(57) ABSTRACT

The invention relates to oxazolopyrimidine compounds of formula I, where A, $R^1$ and $R^2$ are defined as stated in the claims. The compounds of formula I are suitable, for example, for wound healing.

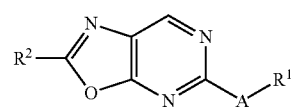

13 Claims, No Drawings

2,5-SUBSTITUTED OXAZOLOPYRIMIDINE DERIVATIVES

The present invention relates to 2,5-substituted oxazolopyrimidine derivatives, and to physiologically acceptable salts thereof.

Structurally similar compounds are already described in the prior art (see WO 2009/154775), which are suitable for treating multiple sclerosis. The mode of action of these compounds consists in causing a desensitization of the EDG-1 signal pathway by activating the EDG-1 receptor (so-called superagonism), which is then equivalent to a functional antagonism of the EDG-1 signal pathway. Systemically means that especially on lymphocytes, the EDG-1 signal pathway is permanently suppressed, as a result of which these cells can no longer chemotactically follow the S1P gradient between blood and lymph fluid. This means that the affected lymphocytes can no longer leave the secondary lymphatic tissue (increased homing) and the number of freely circulating lymphocytes in the plasma is greatly reduced. This deficiency of lymphocytes in the plasma (lymphopenia) brings about immunosuppression which is obligatorily required for the mechanism of action of the EDG-1 receptor modulators described in WO 2009/154775.

The object of the present invention was to provide compounds which are suitable specifically for wound healing and in particular for the treatment of wound healing disorders in patients with diabetes. In addition, it was desirable to provide compounds which are suitable for the treatment of diabetic foot syndrome (DFS). Furthermore, it was desirable to achieve a reproducible activation of the EDG-1 receptor signal pathway which thereby permits, in pharmacological terms, a persistent activation of the EDG-1 signal pathway.

The present invention relates to oxazolopyrimidine compounds of the formula I,

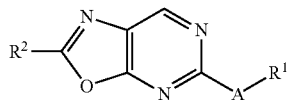

in which A, $R^1$ and $R^2$ are defined as indicated below. The mechanism of action of the compounds of the formula I is thus not based on desensitization of the EDG-1 signal pathway and is therefore in diametral opposition to the mechanism of action described in WO 2009/154775. The invention furthermore relates to processes for the preparation of compounds of the formula I, their use, in particular as active ingredients in pharmaceuticals, and pharmaceutical compositions comprising them.

Compared with healthy people, patients with diabetes have delayed wound healing and an increased rate of infection, especially in the case of long-term hyperglycemia, caused for example by poor blood sugar regulation. The causes include circulation disorders, especially in the area of the small vessels, which lead to impaired oxygen and nutrient supply of the tissue. Moreover, the cell division and cell migration rate of keratinocytes, fibroblasts and dermal endothelial cells is reduced. Additionally, the activity of various defense cells (granulocytes) with reduced phagocytosis (engulfing and destruction of bacteria) is restricted. The function of the antibodies (immunoglobulins) against bacteria is also restricted in the event of high blood sugar values. Accordingly, wounds and infections in patients with diabetes have to be cared for in a particular way.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although S1P is also described as an intracellular messenger, numerous cellular responses of S1P are mediated via the activation of Edg receptors. S1P is generated by the enzyme family of sphingosine kinases (SPHK) and degraded by different phosphatases or lyases.

A subject of the present invention is an oxazolopyrimidine compound of the formula I, in any of its stereoisomeric forms, or a mixture of stereoisomeric forms in any ratio, or a physiologically acceptable salt thereof, or a physiologically acceptable solvate of any of them,

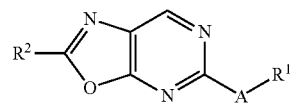

wherein

A is chosen from NH, O and S;

$R^1$ is chosen from $(C_1-C_6)$-alkyl, $(C_2-C_6)$-alkenyl, $(C_2-C_6)$-alkynyl, $(C_3-C_7)$-cycloalkyl-$C_uH_{2u}$— and Het-$C_vH_{2v}$—, wherein u and v are chosen from 1 and 2, or $R^1$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{11}$;

$R^2$ is chosen from phenyl and a residue of an aromatic, 5-membered to 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenyl and residue of an aromatic heterocycle are optionally substituted on one or more ring carbon atoms by identical or different substituents $R^{22}$;

$R^{11}$ is chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di$((C_1-C_4)$-alkyl)aminosulfonyl;

$R^{21}$ is chosen from $(C_1-C_4)$-alkyl, $(C_3-C_7)$-cycloalkyl-$C_wH_{2w}$— and oxy, wherein w is chosen from 0, 1 and 2;

$R^{22}$ is chosen from halogen, hydroxy, $(C_1-C_4)$-alkyl-, $(C_1-C_4)$-alkyloxy, $(C_1-C_4)$-alkyl-S$(O)_m$-, amino, nitro, cyano, hydroxycarbonyl, $(C_1-C_4)$-alkyloxycarbonyl, aminocarbonyl, aminosulfonyl, $R^{23}$ and $R^{23}$—O—;

$R^{23}$ is a residue of a saturated 3-membered to 7-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a ($C_1$-$C_4$)-alkyl substituent and one of the ring sulfur atoms can carry one or two oxo groups, and wherein the residue of a ring is optionally substituted on one or more ring carbon atoms by identical or different substituents $R^{24}$;

$R^{24}$ is chosen from halogen, ($C_1$-$C_4$)-alkyl, hydroxy and oxo;

Het is a residue of a saturated, 4-membered to 7-membered, monocyclic heterocycle which comprises 1 or 2 identical or different ring heteroatoms chosen from N, O and S and which is bonded via a ring carbon atom, wherein the residue of a heterocycle is optionally substituted by one or more identical or different substituents chosen from fluorine and ($C_1$-$C_4$)-alkyl;

m is chosen from 0, 1 and 2, wherein all numbers m are independent of each other; wherein all cycloalkyl groups, independently of each other and independently of any other substituents, are optionally substituted by one or more identical or different substituents chosen from fluorine and ($C_1$-$C_4$)-alkyl;

wherein all alkyl, $C_uH_{2u}$, $C_vH_{2v}$, $C_wH_{2w}$, alkenyl and alkynyl groups, independently of each other and independently of any other substituents, are optionally substituted by one or more fluorine substituents.

Structural elements such as groups, substituents, hetero ring members, numbers or other features, for example alkyl groups, groups like $R^{22}$ or $R^{11}$, numbers like m, u and v, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl-O— groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

As far as applicable, the preceding explanations regarding alkyl groups apply correspondingly to divalent alkyl groups such as the groups $C_uH_{2u}$, $C_vH_{2v}$ and $C_wH_{2w}$, which thus can likewise be linear and branched. Examples of divalent alkyl groups are —$CH_2$— (=methylene), —$CH_2$—$CH_2$—, —$CH_2$—$CH_2$—$CH_2$—, —$CH(CH_3)$—, —$C(CH_3)_2$—, —$CH(CH_3)$—$CH_2$—, —$CH_2$—$CH(CH_3)$—. If a number in a divalent group such as the number u in the group $C_uH_{2u}$, for example, is 0 (=zero), the two groups which are attached to the contemplated group, such as $C_uH_{2u}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. Examples of cycloalkyl groups are cyclopropyl, cyclobutyl, cyclopentyl, cyclohexyl and cycloheptyl. Independently of one another and independently of any other substituents, cycloalkyl groups are optionally substituted by one or more identical or different ($C_1$-$C_4$)-alkyl substituents which can be located in any positions, i.e., cycloalkyl groups can be unsubstituted by alkyl substituents or substituted by alkyl substituents, for example by 1, 2, 3 or 4, or by 1 or 2, ($C_1$-$C_4$)-alkyl substituents, for example by methyl groups. Examples of alkyl-substituted cycloalkyl groups are 4-methylcyclohexyl, 4-tert-butylcyclohexyl or 2,3-dimethylcyclopentyl. Examples of cycloalkylalkyl groups, which can represent groups such as ($C_3$-$C_7$)-cycloalkyl, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, alkynyl groups and cycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —$CF_2$—, —$CF_2$—$CH_2$—, —$CH_2$—$CF_2$—, —$CF_2$—$CF_2$—, —$CF(CH_3)$—, —$C(CF_3)_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy. In one embodiment of the invention, the total number of fluorine substituents and ($C_1$-$C_4$)-alkyl substituents, which independently of any other substituents are optionally present on cycloalkyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on the carbon atoms and/or on such ring nitrogen atoms. In one embodiment of the invention, substituents on such ring nitrogen atoms are chosen from ($C_1$-$C_4$)-alkyl groups, i.e. such ring nitrogen atoms in aromatic heterocycles carry a hydrogen atom or a ($C_1$-$C_4$)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing $R^2$, can also carry an oxy substituent and be present as an N-oxide, and such ring nitrogen atoms can also be present as quaternary salt, for example as N—($C_1$-$C_4$)-alkyl salt such as N-methyl salt, wherein in one embodiment of the invention the counter anion in such quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

In residues of aromatic heterocycles representing $R^1$ or $R^2$, which may be designated as heteroaryl groups, as well as in all other heterocyclic rings in the compounds of the formula I including the group Het and non-aromatic heterocyclic groups representing $R^1$, the ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including Het and non-aromatic groups representing $R^1$, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituents can be located in the 2-position and/or 4-position and/or 5-position and/or 6-position, in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,2,4]triazine, [1,3,5]triazine, [1,3]dithiine, [1,4]dithiine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophene, [1,8]naphthyridine and other naphthyridines, pteridine, and the respective saturated and partially unsaturated heterocycles in which one or more, for example one, two, three, four or all double bonds within the ring system including double bonds in aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4]-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]-heptyl including 2-oxa-5-azabicyclo[2.2.1]-hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O)(=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts. Thus, the compounds of the formula I which contain an acidic group, such as a hydroxycarbonyl group (=carboxy group=C(O)—OH group), can be present on such groups, and can be used according to the invention, as alkaline metal salts, alkaline earth metal salts or as ammonium salts, for example. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I which contain a basic group, i.e. a group which can be protonated such as an amino group or a nitrogen heterocycle, can be present on such groups, and can be used according to the invention, in the form of their addition salts with inorganic and organic acids. Examples of suitable acids include hydrogen chloride, hydrogen bromide, phosphoric acid, sulfuric acid, methanesulfonic acid, oxalic acid, acetic acid, trifluoroacetic acid, tartaric acid, lactic acid, benzoic acid, malonic acid, fumaric acid, maleic acid, citric acid, and other acids known to the person skilled in the art. If a compound of the formula I simultaneously contains an acidic group and a basic group in the molecule, the compound also includes, in addition to the salt forms mentioned, inner salts (=betaines, zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salt. The invention also includes all salts of the compounds of the formula I which, owing to low physiological compatibility of the salt-forming acid or base, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In one embodiment of the invention, A is chosen from NH and O, in another embodiment, A is chosen from NH and S, in another embodiment A is chosen from O and S, in another embodiment A is NH, in another embodiment A is O, in another embodiment A is S.

In one embodiment of the invention, $R^1$ is chosen from $(C_1-C_6)$-alkyl, $(C_2-C_6)$-alkenyl and $(C_2-C_6)$-alkynyl, in another embodiment $R^1$ is $(C_1-C_6)$-alkyl, in another embodiment $R^1$ is $(C_2-C_5)$-alkyl, and in another embodiment $R^1$ is $(C_1-C_4)$-alkyl, provided that $R^1$ cannot be an alkyl group if A is S. In another embodiment $R^1$ is chosen from $(C_1-C_6)$-alkyl, $(C_3-C_7)$-cycloalkyl-$C_uH_{2u}$— and Het-$C_vH_{2v}$—, in another embodiment from $(C_3-C_7)$-cycloalkyl-$C_uH_{2u}$— and Het-$C_vH_{2v}$—, in another embodiment $R^1$ is $(C_3-C_7)$-cycloalkyl-$C_uH_{2u}$—, and in another embodiment $R^1$ is Het-$C_vH_{2v}$—, wherein in this embodiment u and v independently of each other are chosen from 1 and 2. In one embodiment u is 1, in another embodiment u is 2. In one embodiment v is 1, in another embodiment v is 2. In one embodiment, the group $(C_3-C_7)$-cycloalkyl-$C_uH_{2u}$-representing $R^1$ is chosen from cyclopropyl-$C_uH_{2u}$—, cyclobutyl-$C_uH_{2u}$— and cyclopentyl-$C_uH_{2u}$.

In one embodiment, $R^1$ is chosen from $(C_3-C_7)$-cycloalkyl-$C_uH_{2u}$— and Het-$C_vH_{2v}$—, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{11}$, and in another embodiment $R^1$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{11}$. In one embodiment, the number of ring heteroatoms in the ring representing $R^1$ is 0, 1, 2 or 3, in another embodiment it is 0, 1 or 2, in another embodiment it is 0 or 1, in another embodiment it is 0, in another embodiment it is 1, 2, 3 or 4, in another embodiment it is 1, 2 or 3, in another embodiment it is 1 or 2, in another embodiment it is 1. The residue of the ring representing $R^1$ can thus be carbocyclic or heterocyclic. In one embodiment, the ring heteroatoms in $R^1$ are chosen from N and O, in another embodiment from N and S, in another embodiment from O and S, in another embodiment they are N, wherein ring nitrogen atoms can carry a hydrogen atom or a $(C_1-C_4)$-alkyl substituent as occurs in saturated or partially unsaturated heterocycles or in 5-membered aromatic rings in heterocycles such as pyrrole or benzoimidazole, for example, or not carry a hydrogen atom or a $(C_1-C_4)$-alkyl substituent as occurs in aromatic heterocycles such as imidazole or pyridine, for example. In a residue of a heterocycle representing $R^1$ which comprises one or more ring sulfur atoms, in one embodiment one of the ring sulfur atoms is non-oxidized or carries one or two oxo groups, and any other ring sulfur atoms are non-oxidized. The residue of a monocyclic or bicyclic ring representing $R^1$ can be bonded to the group A via any suitable ring carbon atom or ring nitrogen atom. In one embodiment it is bonded via a ring carbon atom, in another embodiment it is bonded via a ring carbon atom or, in case A is NH, via a ring nitrogen atom, and in another embodiment it is bonded via a ring nitrogen atom. The residue of a monocyclic or bicyclic ring representing $R^1$ can be unsaturated and in this case contain 1, 2, 3, 4 or 5, or 1, 2, 3 or 4, or 1, 2 or 3, or 1 or 2, or 1, double bonds within the ring and can in any of the one or two rings be aromatic or non-aromatic, or it can be saturated and in this latter case contain no double bonds within the ring. In one embodiment, the residue of the ring representing $R^1$ is saturated or aromatic, in another embodiment it is saturated, and in another embodiment it is aromatic. In one embodiment, the residue of 3-membered or 4-membered ring representing $R^1$ is saturated. If $R^1$ comprises ring nitrogen atoms which can carry a hydrogen atom or a $(C_1-C_4)$-alkyl substituent, one of such ring nitrogen atoms or two of such ring nitrogen atoms can be present. In one embodiment, the number of optional substituents $R^{11}$ on ring carbon atoms in the ring representing $R^1$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1.

The ring which can represent $R^1$ can be 3-membered, 4-membered, 5-membered, 6-membered, 7-membered, 8-membered, 9-membered or 10 membered. In one embodiment, $R^1$ is 4-membered to 10-membered, in another embodiment 4-membered to 9-membered, in another embodiment 4-membered to 8-membered, in another embodiment 4-membered to 7-membered, in another 5-membered to 7-membered, in another embodiment 5-membered or 6-membered, in another embodiment 6-membered, in another embodiment 8-membered to 10-membered, in another embodiment 9-membered to 10-membered. In one embodiment, a 3-membered ring representing $R^1$ does not comprise any ring heteroatoms. In one embodiment, $R^1$ is monocyclic, in another embodiment bicyclic. In one embodiment, a bicyclic group representing $R^1$ is at least 7-membered. Among others, the residue of a ring representing $R^1$ can be a cycloalkyl group, a phenyl group, a naphthyl group, a residue of an unsaturated, aromatic or non-aromatic heterocyclic group or a residue of a saturated heterocyclic group, which all are optionally substituted on ring carbon atoms and ring nitrogen atoms as specified with respect to $R^1$. As far as applicable, all explanations given above with respect to such groups apply correspondingly to $R^1$. Another example of groups which can represent $R^1$, are cycloalkenyl groups such as $(C_5-C_7)$-cycloalkenyl groups which can be bonded via any ring carbon atom and are optionally substituted as specified with respect to $R^1$. In one embodiment, optional substituents $R^{11}$ on a cycloalkenyl group representing $R^1$ are chosen from fluorine and $(C_1-C_4)$-alkyl. In one embodiment, cycloalkenyl groups contain one double bond within the ring which can be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of residues of rings, from any one or more of which $R^1$ is chosen in one embodiment of the invention, are cyclobutyl, cyclopentyl, cyclohexyl, phenyl, oxetanyl including oxetan-3-yl, tetrahydrofuranyl including tetrahydrofuran-3-yl, tetrahydrothiophenyl including tetrahydrothiophen-3-yl, tetrahydropyranyl including tetrahydropyran-4-yl, azetidinyl including azetidin-1-yl, pyrrolidinyl, piperidinyl, imidazolidinyl, piperazinyl, morpholinyl including Morpholin-1-yl, thiomorpholinyl, furanyl including furan-3-yl, thiophenyl including thiophen-3-yl, pyrazolyl including pyrazol-3-yl, imidazolyl, thiazolyl including thiazol-2-yl, pyridinyl including pyridin-2-yl, pyridin-3-yl and pyridin-4-yl, pyridazinyl including pyridazin-3-yl, wherein in all of them, if applicable, one or two of the ring nitrogen atoms can carry a hydrogen atom or $(C_1-C_4)$-alkyl, and wherein all of them are optionally substituted on one or more ring carbon atoms by identical or different substituents $R^{11}$, and wherein in all of them, if applicable, a ring sulfur atom can be non-oxidized, i.e. be present as a sulfur atom, or carry one or two oxo groups, i.e. be present in the form of a sulfoxide or sulfone.

In one embodiment, $R^1$ is chosen from phenyl and a residue of a saturated or unsaturated 3-membered to 7-membered, monocyclic ring, in another embodiment from phenyl and a residue of a saturated or unsaturated 5-membered to 7-membered, monocyclic ring, in another embodiment from phenyl, pyridinyl and a residue of a saturated 3-membered to 7-membered, monocyclic ring, in another embodiment from phenyl, pyridinyl and a residue of a saturated 5-membered to 7-membered, monocyclic ring, in another embodiment from phenyl and a residue of a saturated 3-membered to 7-membered, monocyclic ring, in another embodiment from phenyl and a residue of a saturated 5-membered to 7-membered, monocyclic ring, wherein in all these embodiments the monocyclic ring comprises 1 or 2 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the phenyl, pyridinyl and residue of a ring are optionally substituted on one or more ring carbon atoms by identical or different substituents $R^{11}$, and wherein pyridinyl includes pyridin-2-yl, pyridin-3-yl and pyridin-4-yl. In another embodiment, $R^1$ is chosen from phenyl and pyridinyl, in another embodiment $R^1$ is pyridinyl, and in another embodiment $R^1$ is phenyl, wherein in these embodiments pyridinyl includes the groups pyridin-2-yl, pyridin-3-yl and pyridin-4-yl and in one embodiment is chosen from any one or more of these groups, and wherein in all these embodiments the phenyl and the pyridinyl are optionally substituted on one or more ring carbon atoms by identical or different substituents $R^{11}$.

In one embodiment of the invention, the number w is chosen from 0 and 1, in another embodiment it is 0, in another embodiment it is 1. In one embodiment, a $(C_3-C_7)$-cycloalkyl group present in $R^{21}$ is $(C_3-C_6)$-cycloalkyl, in another embodiment $(C_3-C_5)$-cycloalkyl, in another embodiment cyclopropyl. In one embodiment, $R^{21}$ is chosen from $(C_1-C_4)$-alkyl and oxy, in another embodiment $R^{21}$ is $(C_1-C_4)$-alkyl, in another embodiment it is $(C_1-C_3)$-alkyl, in another embodiment it is methyl, and in another embodiment it is oxy.

In one embodiment of the invention, the number of ring heteroatoms in an aromatic heterocycle representing $R^2$ is 1 or 2, in another embodiment it is 1. In one embodiment of the invention, $R^2$ is chosen from phenyl and a residue of an aromatic, 6-membered monocyclic heterocycle which comprises 1, 2 or 3 ring nitrogen atoms, in another embodiment 1 or 2 ring nitrogen atoms, in another embodiment 1 ring nitrogen atom, wherein one of the ring nitrogen atoms can carry a substituent $R^{21}$ which is oxy, i.e. wherein one of the ring nitrogen atoms can be oxidized to the N-oxide, and wherein the phenyl and residue of an aromatic heterocycle are optionally substituted on one or more ring carbon atoms by identical or different substituents $R^{22}$. In another embodiment, $R^2$ is phenyl, wherein the phenyl is optionally substituted on one or more ring atoms by identical or different substituents $R^{22}$, and in another embodiment $R^2$ is pyridinyl, wherein the ring nitrogen atom can carry a substituent $R^{21}$ which is oxy, i.e. wherein the ring nitrogen atom can be oxidized to the N-oxide, and wherein the pyridinyl is optionally substituted on one or more ring carbon atoms by identical or different substituents $R^{22}$. In another embodiment, $R^2$ is a residue of an aromatic 5-membered heterocycle which comprises 1, 2 or 3 identical or different ring heteroatoms chosen from N, O and S, wherein one of the ring nitrogen atoms can carry a hydrogen atom or a substituent $R^{21}$, and wherein the residue of an aromatic heterocycle is optionally substituted on one or more ring carbon atoms by identical or different substituents $R^{22}$. In one embodiment, a residue of an aromatic heterocyclic group representing $R^2$ is chosen from furanyl, thiophenyl, oxazolyl, thiazolyl, pyridinyl, pyridazinyl, pyrimidinyl and pyrazinyl, in another embodiment from furanyl, thiophenyl, thiazolyl, pyridinyl, pyridazinyl, pyrimidinyl and pyrazinyl, in another embodiment from furanyl, thiophenyl, pyridinyl, pyridazinyl, pyrimidinyl and pyrazinyl, in another embodiment from furanyl, thiophenyl, pyridinyl and pyrimidinyl, in another embodiment from furanyl, thiophenyl and pyridinyl, which are all optionally substituted as indicated with respect to $R^2$. In another embodiment, $R^2$ is chosen from one or more of the groups furan-2-yl, thiophen-2-yl, pyridin-3-yl, pyridin-4-yl and pyrimidin-5-yl, in another embodiment from phenyl, furan-2-yl, thiophen-2-yl, pyridin-3-yl, pyridin-4-yl and pyrimidin-5-yl, in another embodiment from pyridin-3-yl and pyridin-4-yl, in another embodiment from phenyl, pyridin-3-yl and pyridin-4-yl, which all are optionally substituted as indicated with respect to $R^2$. In one embodiment, the number of substituents $R^{22}$ which are optionally present on ring carbon atoms in $R^2$, is 1, 2, 3, 4 or 5, in another embodiment 1, 2, 3 or 4, in another embodiment 1, 2 or 3, in another embodiment 1 or 2, in another embodiment 1. Ring carbon atoms in $R^2$ which do not carry a substituent $R^{22}$, carry a hydrogen atom.

In one embodiment of the invention, $R^{11}$ is chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$-, amino, $(C_1-C_4)$-alkylamino, di$((C_1-C_4)$-alkyl)amino, cyano, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxy and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxy and $(C_1-C_4)$-alkyloxy, wherein in all these embodiments all alkyl groups independently of each other are optionally substituted by one or more fluorine substituents.

In one embodiment, the optional substituents $R^{11}$ on the residue of an aromatic ring representing $R^1$, for example on a phenyl group or pyridinyl group representing $R^1$, are chosen from halogen, $(C_1-C_4)$-alkyl, $(C_3-C_7)$-cycloalkyl, hydroxy, $(C_1-C_4)$-alkyloxy, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, $(C_1-C_4)$-alkyl-$S(O)_m$—, amino, $(C_1-C_4)$-alkylamino, di$((C_1-C_4)$-alkyl)amino, cyano, anninosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, $(C_1-C_4)$-alkyl-$S(O)_m$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxy and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxy and $(C_1-C_4)$-alkyloxy, wherein in all these embodiments all alkyl groups independently of each other are optionally substituted by one or more fluorine substituents.

In one embodiment, the optional substituents $R^{11}$ on the residue of a saturated or non-aromatic unsaturated ring representing $R^1$ are chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4$-alkylsulfonylamino and cyano, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino, di$((C_1-C_4)$-alkyl)amino and cyano, in another embodiment from halogen, $(C_1-C_4)$-alkyl, $(C_3-C_7)$-cycloalkyl, hydroxy, $(C_1-C_4)$-alkyloxy and oxo, in another embodiment from halogen, $(C_1-C_4)$-alkyl, hydroxy, $(C_1-C_4)$-alkyloxy and oxo, in another embodiment from fluorine, chlorine, $(C_1-C_4)$-alkyl, hydroxy, $(C_1-C_4)$-alkyloxy and oxo, in another embodiment from $(C_1-C_4)$-alkyl, hydroxy and oxo, in another embodiment from alkyl and hydroxy, and in another embodiment they are $(C_1-C_4)$-alkyl, wherein in all these embodiments all alkyl groups independently of each other are optionally substituted by one or more fluorine substituents. In case the residue of a ring representing $R^1$ contains any oxo groups as substituents $R^{11}$, in one embodiment not more than two such oxo substituents are present, and in another embodiment not more than one such oxo substituent is present.

In one embodiment of the invention, the substituents $R^{22}$ which are optionally present on the group $R^2$, are chosen from halogen, hydroxy, $(C_1-C_4)$-alkyl-, $(C_1-C_4)$-alkyloxy-, $(C_1-C_4)$-alkyl-$S(O)_m$—, amino, nitro, cyano, $R^{23}$ and $R^{23}$—O—, in another embodiment from halogen, hydroxy, $(C_1-C_4)$-alkyloxy-, amino, cyano, $R^{23}$ and $R^{23}$—O—, in another embodiment from halogen, hydroxy, $(C_1-C_4)$-alkyl-, $(C_1-C_4)$-alkyloxy-, $R^{23}$ and $R^{23}$—O—, in another embodiment from halogen, hydroxy, $(C_1-C_4)$-alkyl- and $(C_1-C_4)$-alkyloxy-, wherein in all these embodiments $R^{23}$ is as defined.

In one embodiment, 1, 2 or 3 of the substituents $R^{22}$, in another embodiment 1 or 2 of the substituents $R^{22}$, and in another embodiment 1 of the substituents $R^{22}$, which are optionally present on the group $R^2$, are defined as in the general definition of $R^{22}$ and thus are chosen from halogen, hydroxy, $(C_1-C_4)$-alkyl-, $(C_1-C_4)$-alkyloxy-, alkyl-$S(O)_m$—, amino, nitro, cyano, hydroxycarbonyl, $(C_1-C_4)$-alkyloxycarbonyl, aminocarbonyl, aminosulfonyl, $R^{23}$ and $R^{23}$—O—, wherein $R^{23}$ is as defined, and any further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1-C_4)$-alkyl-, $(C_1-C_4)$-alkyloxy-, $(C_1-C_4)$-alkyl-$S(O)_m$—, amino, nitro, cyano, $R^{23}$ and $R^{23}$—O—, wherein all alkyl groups independently of each other are optionally substituted by one or more fluorine substituents as generally applies to alkyl groups. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are chosen from halogen, hydroxy, $(C_1-C_4)$-alkyloxy-, $(C_1-C_4)$-alkyl-S(O)$_m$—, amino, nitro, cyano, $R^{23}$ and $R^{23}$—O—, in another embodiment from halogen, hydroxy, $(C_1-C_4)$-alkyl-S(O)$_m$—, amino, $R^{23}$ and $R^{23}$—O—, in another embodiment from halogen, hydroxy, $(C_1-C_4)$-alkyl-, $(C_1-C_4)$-alkyloxy-, amino, $R^{23}$ and $R^{23}$—O—, in another embodiment from halogen, hydroxy, $(C_1-C_4)$-alkyl-, $(C_1-C_4)$-alkyloxy-, $(C_1-C_4)$-alkyl-S(O)$_m$-, amino and cyano, in another embodiment from halogen, hydroxy, $(C_1-C_4)$-alkyl-, $(C_1-C_4)$-alkyloxy- and cyano, wherein $R^{23}$ is as defined. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are not located on ring carbon atoms within the group $R^2$ which are adjacent to the atom via which the group $R^2$ is bonded to the oxazolopyrimidine ring depicted in formula I. In another embodiment, in the case of a phenyl group representing $R^2$, 1 or 2 such substituents $R^{22}$, or 1 such substituent $R^{22}$, is optionally present in any of positions 3, 4 and 5 of the phenyl group, and in another embodiment 1 such substituent $R^{22}$ is present in position 4 of the phenyl group. In one embodiment, the said further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1-C_4)$-alkyl-, $(C_1-C_4)$-alkyloxy-, $(C_1-C_4)$-alkyl-S(O)$_m$—, amino and cyano, in another embodiment from halogen, hydroxy, $(C_1-C_4)$-alkyl-, $(C_1-C_4)$-alkyloxy-, amino and cyano, in another embodiment from halogen, hydroxy, $(C_1-C_4)$-alkyloxy- and cyano, in another embodiment from halogen, $(C_1-C_4)$-alkyl- and $(C_1-C_4)$-alkyloxy-, in another embodiment from halogen and $(C_1-C_4)$-alkyl-, wherein in all these embodiments all alkyl groups independently of each other are optionally substituted by one or more fluorine substituents.

In one embodiment of the invention, $R^{23}$ is a residue of a monocyclic ring, in another embodiment a residue of a bicyclic ring. The residue of a ring representing $R^{23}$ can be carbocyclic or heterocyclic. In one embodiment, the residue of a monocyclic ring representing $R^{23}$ is carbocyclic, in another embodiment heterocyclic. In one embodiment, the residue of a bicyclic ring representing $R^{23}$ is carbocyclic, in another embodiment heterocyclic. In one embodiment of the invention, the number of ring heteroatoms in $R^{23}$ is 0, 1, 2 or 3, in another embodiment 0, 1 or 2, in another embodiment 0 or 1, in another embodiment 1, 2, 3 or 4, in another embodiment 1, 2 or 3, in another embodiment 1 or 2, in another embodiment 1, and in another embodiment it is 0, and in this latter embodiment $R^{23}$ thus is a $(C_3-C_7)$-cycloalkyl group. In one embodiment, the residue of a monocyclic ring representing $R^{23}$ is an oxetanyl group, for example oxetan-3-yl.

In one embodiment, the ring heteroatoms in $R^{23}$ are chosen from N and O, in another embodiment from O and S, in another embodiment they are N, and in another embodiment they are O, wherein ring nitrogen atoms can carry a hydrogen atom or a $(C_1-C_4)$-alkyl substituent. $R^{23}$ can be bonded via any suitable ring carbon atom and ring nitrogen atom. In case $R^{23}$ is bonded to an oxygen atom, in one embodiment $R^{23}$ is bonded via a ring carbon atom. In another embodiment, $R^{23}$ is bonded via a ring carbon atom irrespective of the atom to which $R^{23}$ is bonded. In another embodiment, $R^{23}$ is bonded via a ring nitrogen atom. In one embodiment, the number of optional substituents $R^{24}$ on ring carbon atoms in $R^{23}$ is 1, 2, 3 or 4 or 5, in another embodiment 1, 2, 3 or 4, in another embodiment 1, 2 or 3, in another embodiment 1 or 2, in another embodiment 1. $R^{23}$ can be 3-membered, 4-membered, 5-membered, 6-membered or 7-membered. In one embodiment, $R^{23}$ is 4-membered to 7-membered, in another embodiment 4-membered to 6-membered, in another embodiment 5-membered to 6-membered, in another embodiment 4-membered to 5-membered. In one embodiment, a 3-membered ring representing $R^{23}$ does not comprise any ring heteroatoms. Examples of residues of rings from any one or more of which $R^{23}$ is chosen in one embodiment of the invention, are oxetan-3-yl, azetidin-1-yl, pyrrolidin-1-yl, piperidin-1-yl, piperidin-4-yl, morpholin-4-yl and piperazin-1-yl, which are all optionally substituted as indicated. In one embodiment, $R^{23}$ is chosen from any one or more of the residues oxetan-3-yl, pyrrolidin-1-yl, piperidin-1-yl, morpholin-4-yl and piperazin-1-yl, in another embodiment from any one or more of the residues oxetan-3-yl, azetidin-1-yl, morpholin-4-yl and piperazin-1-yl, in another embodiment from any one or more of the residues oxetan-3-yl, azetidin-1-yl, pyrrolidin-1-yl, and piperidin-1-yl, and in another embodiment $R^{23}$ is oxetan-3-yl, which are all optionally substituted as indicated.

In one embodiment of the invention, $R^{24}$ is chosen from halogen, $(C_1-C_4)$-alkyl, and hydroxy, in another embodiment from fluorine, $(C_1-C_4)$-alkyl and hydroxy, in another embodiment from fluorine, methyl and hydroxy, in another embodiment from fluorine and methyl, in another embodiment from methyl and hydroxy, in another embodiment from fluorine, $(C_1-C_4)$-alkyl, hydroxy and oxo.

In one embodiment of the invention, the ring heteroatoms in Het are chosen from N and O, in another embodiment from O and S, in another embodiment they are O atoms. In another embodiment, the number of ring heteroatoms in Het is 1. In one embodiment, two ring oxygen atoms in Het are not present in adjacent ring positions, in another embodiment two ring heteroatoms chosen from O and S are not present in adjacent ring positions, in another embodiment two ring heteroatoms are not present in adjacent ring positions. Ring nitrogen atoms in Het carry a hydrogen atom or a substituent as specified. In one embodiment, optional substituents on ring nitrogen atoms in Het are $(C_1-C_4)$-alkyl substituents. In one embodiment, optional substituents on ring nitrogen atoms and ring carbon atoms in Het are $(C_1-C_4)$-alkyl substituents. In one embodiment, the number of optional substituents on Het is 1, 2, 3, 4 or 5, in another embodiment 1, 2, 3 or 4, in another embodiment 1, 2 or 3, in another embodiment 1 or 2, in another embodiment 1. Het can be bonded via any suitable ring carbon atom. In one embodiment, Het is bonded via a ring carbon atom which is not adjacent to a ring heteroatom. Het can be 4-membered, 5-membered, 6-membered or 7-membered. In one embodiment, Het is 4-membered or 5-membered, in another embodiment 5-membered to 7-membered, in another embodiment 5-membered or 6-membered, in another embodiment 4-membered. Examples of Het, from any one or more of which Het is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidinyl-2-yl and pyrrolidinyl-3-yl, piperidinyl including piperidinyl-2-yl, piperidinyl-3-yl and piperidinyl-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, which all are optionally substituted as specified with respect to Het.

A subject of the invention are all compounds of the formula I wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

An example of compounds of the invention which with respect to any structural elements are defined as in specified embodiments of the invention or definitions of such elements, and which are a subject of the invention, are compounds of the formula I, wherein A is chosen from O and S;

$R^1$ is chosen from $(C_3-C_7)$-cycloalkyl-$C_uH_{2u}$— and Het-$C_vH_{2v}$—, wherein u and v are chosen from 1 and 2, or $R^1$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{11}$;

$R^2$ is chosen from phenyl and pyridinyl, wherein the ring nitrogen atom of the pyridinyl can carry an oxy substituent, and wherein the phenyl and the pyridinyl are optionally substituted on one or more ring carbon atoms by identical or different substituents $R^{22}$;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

Another such example are compounds of the formula I, wherein

A is O;

$R^1$ is chosen from $(C_3-C_7)$-cycloalkyl-$C_uH_{2u}$— and Het-$C_vH_{2v}$—, wherein u and v are chosen from 1 and 2, or $R^1$ is a residue of a saturated, 3-membered to 7-membered, monocyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{11}$;

$R^2$ is chosen from phenyl and pyridinyl, wherein the ring nitrogen atom of the pyridinyl can carry an oxy substituent, and wherein the phenyl and the pyridinyl are optionally substituted on one or more ring carbon atoms by identical or different substituents $R^{22}$;

$R^{11}$ is chosen from halogen, $(C_1-C_4)$-alkyl, $(C_1-C_4)$-alkyloxy and cyano;

$R^{22}$ is chosen from halogen, hydroxy, $(C_1-C_4)$-alkyl-, $(C_1-C_4)$-alkyloxy, cyano, $R^{23}$ and $R^{23}$—O—;

$R^{23}$ is a residue of a saturated 3-membered to 6-membered, monocyclic ring which comprises 0 or 1 ring heteroatom chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{24}$;

$R^{24}$ is chosen from fluorine, $(C_1-C_4)$-alkyl and hydroxy;

Het is a residue of a saturated, 4-membered to 7-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and $(C_1-C_4)$-alkyl;

wherein all cycloalkyl groups, independently of each other and independently of any other substituents, are optionally substituted by one or more identical or different substituents chosen from fluorine and $(C_1-C_4)$-alkyl;

wherein all alkyl, $C_uH_{2u}$ and $C_vH_{2v}$ groups, independently of each other and independently of any other substituents, are optionally substituted by one or more fluorine substituents, in any of their stereoisomeric forms or a mixture of stereoisomeric forms in any ratio, and their physiologically acceptable salts, and the physiologically acceptable solvates of any of them.

Another such example are compounds of the formula I, wherein

A is O;

$R^1$ is is a residue of a saturated or unsaturated, 3-membered to 7-membered, monocyclic ring which comprises 0 or 1 ring heteroatoms chosen from N, O and S, wherein a ring nitrogen atom can carry a hydrogen atom or a $(C_1-C_4)$-alkyl substituent and a ring sulfur atom can carry one or two oxo groups, and wherein the residue of a ring is optionally substituted on one or more ring carbon atoms by identical or different substituents $R^{11}$;

$R^2$ is chosen from phenyl and pyridinyl, wherein the ring nitrogen atom of the pyridinyl can carry an oxy substituent, and wherein the phenyl and the pyridinyl are optionally substituted on one or more ring carbon atoms by identical or different substituents $R^{22}$;

$R^{11}$ is chosen from halogen, $(C_1-C_4)$-alkyl and $(C_1-C_4)$-alkyloxy;

$R^{22}$ is chosen from halogen, hydroxy, $(C_1-C_4)$-alkyl-, $(C_1-C_4)$-alkyloxy, $R^{23}$ and $R^{23}$—O—;

$R^{23}$ is a residue of a saturated 3-membered to 6-membered, monocyclic ring which comprises 0 or 1 ring heteroatom chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{24}$;

$R^{24}$ is chosen from fluorine, $(C_1-C_4)$-alkyl and hydroxy;

wherein all cycloalkyl groups, independently of each other and independently of any other substituents, are optionally substituted by one or more identical or different substituents chosen from fluorine and $(C_1-C_4)$-alkyl;

wherein all alkyl groups, independently of each other and independently of any other substituents, are optionally substituted by one or more fluorine substituents, in any of their stereoisomeric forms or a mixture of stereoisomeric forms in any ratio, and their physiologically acceptable salts, and the physiologically acceptable solvates of any of them.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of any of them. Irrespective thereof whether a specific compound is disclosed herein as a free compound and/or as a specific salt, it is a subject of the invention both in the form of the free compound and in the form of all its physiologically acceptable salts, and if a specific salt is disclosed, additionally in the form of this specific salt, and in the form of the physiologically acceptable solvates of any of them. Thus, a subject of the invention also is a compound of the formula I which is chosen from any one or more of the specific compounds of the formula I disclosed herein, including the example compounds specified below, and the physiologically acceptable salts thereof, and the physiologically acceptable solvates of any of them, wherein the compound of the formula I is a subject of the invention in any of its stereoisomeric forms or as a mixture of stereoisomeric forms in any ratio, if applicable. As an example mentioned is a compound of the formula I, or a physiologically acceptable salt thereof, or a physiologically acceptable solvate of any of them, which is chosen from 5-(2-fluoro-phenoxy)-2-(4-methoxy-3,5-dimethyl-phenyl)-oxazolo[5,4-d]pyrimidine, 4-[5-(2-fluoro-phenoxy)-oxazolo[5,4-d]pyrimidin-2-yl]-2,6-dimethyl-phenol, 5-(2-fluoro-phenoxy)-2-(3-methoxy-phenyl)-oxazolo[5,4-d]pyrimidine, 4-[5-(2-fluoro-phenoxy)-oxazolo[5,4-d]pyrimidin-2-yl]-phenol, 5-(2-fluoro-phenoxy)-2-(4-methoxy-3-methyl-phenyl)-oxazolo[5,4-d]pyrimidine, 5-(2-fluoro-phenoxy)-2-(4-methoxy-3-trifluoromethyl-phenyl)-oxazolo[5,4-d]pyrimidine, 4-[5-(2-fluoro-phenoxy)-oxazolo[5,4-d]pyrimidin-2-yl]-2-methyl-phenol, 2-(4-methoxy-3,5-dimethyl-phenyl)-5-phenoxy-oxazolo[5,4-d]pyrimidine, 2-(4-methoxy-3,5-dimethyl-phenyl)-5-(pyridin-3-yloxy)-oxazolo[5,4-d]pyrimidine, and 4-[5-(2-fluoro-phenoxy)-oxazolo[5,4-d]pyrimidin-2-yl]-2-trifluoromethyl-phenol.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I,

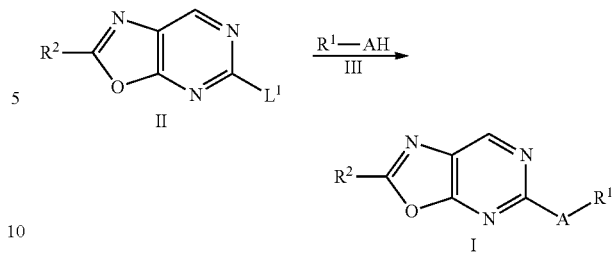

wherein the groups A, $R^1$ and $R^2$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in a nucleophilic aromatic substitution reaction, such as a sulfonyloxy group, for example methanesulfonyloxy or trifluoromethanesulfonyloxy, a halogen atom, for example chlorine or bromine, or a sulfoxide group or a sulfone group, for example a group of the formula —S(O)-Alk or —S(O)$_2$-Alk wherein Alk is a (C$_1$-C$_4$)-alkyl group, for example methyl or ethyl.

The reaction of the compounds of the formulae II and III is a nucleophilic aromatic substitution reaction at the carbon atom in the 5-position of oxazolo[5,4-d]pyrimidine ring, i.e. in the pyrimidine moiety, and can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), a ketone such as acetone or butan-2-one, an ester such as ethyl acetate or butyl acetate, a nitrile such as acetonitrile, an amide such as N,N-dimethylformamide (DMF), N,N-dimethylacetamide (DMA) or N-methylpyrrolidin-2-one (NMP), or a mixture of solvents, at temperatures from about 20° C. to about 160° C., for example at temperatures from about 40° C. to about 100° C., depending on the particulars of the specific case. Generally it is favorable for enhancing the nucleophilicity of the compound of the formula III to add a base, for example a tertiary amine, such as triethylamine, ethyldiisopropylamine or N-methylmorpholine, or an inorganic base such as an alkaline earth metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula III can also be treated with a base and converted into a salt separately before the reaction with the compound of the formula II.

The starting compounds of the formulae II and III can be obtained by procedures described in the literature or analogously to procedures described in the literature, and in many cases are commercially available. For example, the compounds of the formula II can be obtained by reacting a 5-amino-pyrimidine derivative of the formula IV with an activated carboxylic acid derivative of the formula V to give a compound of the formula VI, cyclizing the latter compound with formation of the oxazolo[5,4-d]pyrimidine ring system to give a compound of the formula VII which can already be a compound of the formula II depending on the meaning of R' and L¹, and optionally modifying the group R' in the compound of the formula VII to give a compound of the formula II.

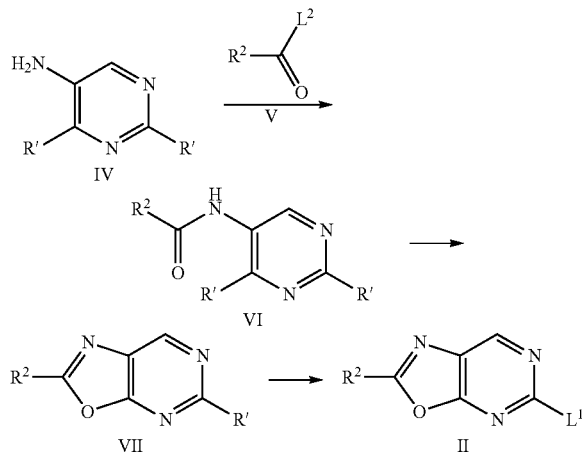

The group $R^2$ in the compounds of the formulae V, VI and VII is defined as in the compounds of the formula I and additionally functional groups can be present in protected form or in the form of a precursor group which is later converted into the final group. The groups R' in the compounds of the formulae IV, VI and VII can be a hydroxy group or a halogen atom, such as chlorine or bromine. The group $L^2$ in the compounds of the formula V is a nucleophilically substitutable leaving group and can in particular be a halogen atom, such as chlorine or bromine, and the compound of the formula V can thus be a carboxylic acid halide. $L^2$ can also be a group of the formula $R^2$—C(O)—O and the compound of the formula V can thus be a carboxylic acid anhydride, for example. Compounds occurring in the synthesis of the compounds of the formula I, such as the compound of the formula IV, may also be present in another tautomeric form, for example in the keto form in case the groups R' in the compound of the formula IV are hydroxy groups. Compounds occurring in the synthesis of the compounds of the formula I, including starting compounds, intermediates and products, can also be employed or obtained in the form of a salt.

The compounds of the formula IV are commercially available or can be obtained according to procedures described in the literature. For example, the compound of the formula IV in which R' is hydroxy, which is the compound 5-amino-uracil in its tautomeric hydroxy form, can be obtained from uracil by nitration to give 5-nitro-uracil, and reduction of the nitro group, for example as described in B. Johnson et al., J. Am. Chem. Soc. 41 (1919), 782-789. The compound of the formula IV in which R' is chlorine, i.e. 5-amino-2,4-dichloro-pyrimidine, can be obtained from 5-nitro-uracil by chlorination, for example by treatment with phosphorus oxychloride, and reduction of the nitro group in the obtained 2,4-dichloro-5-nitro-pyrimidine, for example as described in N. Whittaker, J. Chem. Soc. (1951), 1565-1570.

The reaction of the compounds of the formulae IV and V can be carried out under standard conditions for the acylation of an amine with an activated carboxylic acid derivative like an acid halide or anhydride. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures from about −10° C. to about 40° C., for example at temperatures from about 0° C. to about 30° C. Generally the reaction is carried out with addition of a base, for example a tertiary amine, such as triethylamine, ethyldiisopropylamine or N-methylmorpholine, or an inorganic base such as an alkaline metal hydroxide, carbonate or hydrogencarbonate like sodium hydroxide, potassium hydroxide, sodium carbonate, potassium carbonate or sodium hydrogencarbonate.

In case the group R' in the compound of the formula VI is hydroxy, the cyclization of the compound of the formula VI to the compound of the formula VII can favorably be carried out in the presence of a halogenating agent such as a phosphorus halide, like phosphorus pentachloride or phosphorus oxychloride or a mixture thereof, in an inert solvent, for example a hydrocarbon or chlorinated hydrocarbon such as benzene, toluene, xylene, chlorobenzene, dichloromethane, chloroform or dichloroethane, at temperatures from about 20° C. to about 100° C., for example temperatures from about 50° C. to about 80° C.

In case the group R' in the compound of the formula VI is halogen such as chlorine, the cyclization of the compound of the formula VI to the compound of the formula VII can be carried out thermally, for example by heating the compound of the formula VI in an inert solvent such as a hydrocarbon or chlorinated hydrocarbon, for example toluene, xylene or chlorobenzene, or an amide, for example DMF, DMA or NMP, or a nitrile, for example acetonitrile, to temperatures from about 100° C. to about 200° C., for example to temperatures from about 120° C. to about 180° C., optionally under pressure, and optionally in the presence of a base, such as a tertiary amine, for example triethylamine, ethyldiisopropylamine or N-methylmorpholine, or an inorganic base, for example an alkaline metal hydroxide, carbonate or hydrogencarbonate like sodium hydroxide, potassium hydroxide, sodium carbonate, potassium carbonate or sodium hydrogencarbonate. The thermal cyclization can favorably be performed in a microwave reactor.

The compound of the formula VII can already be a compound of the formula II and employed in the reaction with the compound of the formula III, if it has been obtained from a compound of the formula VI in which R' is halogen, such as chlorine, and the halogen atom in the cyclization product has not been replaced, for example during work-up, or if it has been obtained from a compound of the formula VI in which R' is hydroxy, and concomitantly with the cyclization the second hydroxy group in the compound of the formula VII is halogenated, for example replaced with a chlorine atom as may occur during the cyclization by means of a phosphorus halide. If a compound of the VII, in which R' is hydroxy, is obtained as cyclization product, the hydroxy group can be converted into a leaving group under standard conditions, for example into a halogen atom such as a chlorine atom by treatment with a halogenating agent such as a phosphorus halide, or into a sulfonyloxy group as indicated above by treatment with a sulfonyl chloride or sulfonic acid anhydride. Depending on the particulars of the specific case, such as the reactivity of the specific compound of the formula III which is to be reacted with the compound of the formula II, it can also be advantageous to modify the group R' in a compound of the formula VII even though it already is a leaving group. For example, a compound of the formula VII in which R' is halogen, such as chlorine, can be converted into a compound of the formula II in which $L^1$ is the group —S(O)₂-Alk and which is then reacted with a compound of the formula III, by treatment with an alkanesulfinic acid of the formula Alk-S(O)—OH, wherein Alk is ($C_1$-$C_4$)-alkyl. Such a conversion is generally carried out in the presence of a base, such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, in an inert solvent, such as a hydrocarbon or chlorinated hydrocarbon like benzene, toluene, xylene, chlorobenzene, dichloromethane, chloroform or dichloroethane, an ether such as THF, dioxane, dibutyl ether, diisopropyl ether or DME, an amide such as DMF or NMP, or a mixture of solvents, at temperatures from about 20° C. to about 150° C., for example at temperatures from about 50° C. to about 120° C. An alkanesulfinic acid can also be treated with a base and converted into a salt separately before the reaction with the compound of the formula VII.

Further compounds of the formula I can be obtained from suitable compounds prepared according to the above-described processes by functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be liberated from an ether group by ether cleavage, for example by means of boron tribromide, or from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like DMF or NMP or a ketone like acetone or butan-2-one, or with the respective alcohol under the conditions of the Mitsunobu reaction, i.e. in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane (cf. O. Mitsunobu, Synthesis (1981), 1-28).

A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), O-(cyano(ethoxycarbonyl)methyleneamino)-N,N,N',N'-tetramethyluronium tetrafluoroborate (TOTU), or [(benzotriazol-1-yloxy)-dimethylamino-methylene]-dimethyl-ammonium tetrafluoroborate (TBTU), for example. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed in the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, III, IV, V, VI and VII, wherein A, $R^1$, $R^2$, R', $L^1$ and $L^2$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I also apply correspondingly to the said intermediates and starting compounds. A subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I, optionally in combination with other pharmacologically active compounds, can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiological sodium chloride solution, vegetable oils, waxes, alcohols such as ethanol, isopropanol; 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of an acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing about 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the signals is given. In the MS characterization, in general the mass number (m/z) of the peak of the molecular ion M, e.g. M$^+$, or of a related ion such as the ion M+1, e.g. [M+1]$^+$, i.e. the protonated molecular ion [M+H]$^+$, which was formed depending on the ionization method used, is given. Generally, the ionization method was electrospray ionization (ESI). The LC/MS conditions used were as follows.

Method LC1

Column: UPLC BEH C18, 50×2.1 mm, 1.7 μm; flow: 0.9 ml/min; eluent A: acetonitrile+0.08% formic acid; eluent B: water+0.1% formic acid; gradient: from 5% A+95% B to 95% A+5% B in 1.1 min, then 95% A+5% B for 0.6 min; MS ionization method: ESI$^+$ Method LC2

Column: YMC-Pack J'sphere H80, 33×2.1 mm, 4 μm, flow: 1.0 ml/min; eluent A: acetonitrile+0.05% TFA; eluent B:

water+0.05% TFA; gradient: from 2% A+98% B to 95% A+5% B in 5 min, then 95% A+5% B for 1.25 min; MS ionization method: ESI+

Method LC3

Column: Waters XBridge C18, 50×4.6 mm, 2.5 µm; flow: 1.3 ml/min; eluent A: acetonitrile+0.05% TFA; eluent B: water+0.05% TFA; gradient: 5% A+95% B for 0.3 min, then from 5% A+95% B to 95% A+5% B in 3.2 min, then 95% A+5% B for 0.5 min; MS ionization method: ESI+

EXAMPLE 1

5-(2-Fluoro-phenoxy)-2-(4-methoxy-3,5-dimethyl-phenyl)-oxazolo[5,4-d]pyrimidine

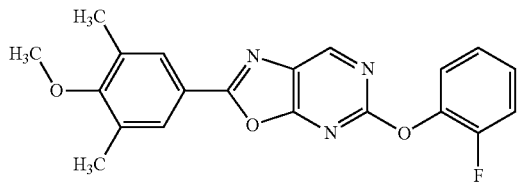 [SMILES: COc1c(C)cc(-c2nc3cnc(Oc4ccccc4F)nc3o2)cc1C]

(a) N-(2,4-Dichloro-pyrimidin-5-yl)-4-methoxy-3,5-dimethyl-benzamide

A solution of 3.2 g of 5-amino-2,4-dichloro-pyrimidine in 50 ml of ethyl acetate was added to a mixture of 25 ml of a saturated aqueous solution of sodium hydrogencarbonate and 25 ml of water. Then a solution of 4.9 g of 3,5-dimethyl-4-methoxybenzoyl chloride was added at room temperature over a period of 15 min. The mixture was mixed intensively for 4 h. Then the layers were separated and the aqueous layer was extracted twice with ethyl acetate. After drying over sodium sulfate and filtration the solvent was removed in vacuo to give 7.54 g of raw product. The raw product was triturated with 25 ml of isopropanol. After filtration and washing with 10 ml of isopropanol, 2.74 g of the title compound were obtained as a white solid.

(b) 5-Chloro-2-(4-methoxy-3,5-dimethyl-phenyl)-oxazolo[5,4-d]pyrimidine A solution of 2.74 g of N-(2,4-dichloro-pyrimidin-5-yl)-4-methoxy-3,5-dimethyl-benzamide and 3.2 ml of N,N-diisopropylethylamine in 17 ml of acetonitrile was split into two batches which were each heated for 1 h to 160° C. in a microwave reactor. The batches were then recombined and the precipitate was isolated by filtration to give 600 mg of the title compound as a dark but quite pure solid (600 mg). The solvents of the mother liquor were removed in vacuo and the residue was subjected to silica gel chromatography (heptane/ethyl acetate gradient) to give another 600 mg of the title compound as a pale yellow solid.

(c) 5-(2-Fluoro-phenoxy)-2-(4-methoxy-3,5-dimethyl-phenyl)-oxazolo[5,4-d]pyrimidine 149 mg of sodium hydride were added under an argon atmosphere to a solution of 418 mg of 2-fluoro-phenol in 15 ml of dimethylacetamide. After stirring for 30 min at room temperature, a solution of 900 mg of 5-chloro-2-(4-methoxy-3,5-dimethyl-phenyl)-oxazolo[5,4-d]pyrimidine in 20 ml of dimethylacetamide was added slowly. The mixture was allowed to stir for 1.5 h at room temperature. Upon consumption of the starting oxazolo[5,4-d]pyrimidine an aqueous solution of citric acid (100 g/l) was added until the pH was neutral. The aqueous layer was extracted twice with 15 ml of ethyl acetate, and the combined organic layers were dried over sodium sulfate, filtered, and the solvents were removed in vacuo. The title compound was isolated by silica gel chromatography (heptane/ethyl acetate gradient). Yield: 820 mg of a white solid.

LC/MS (method LC3): Rt=3.56 min; m/z=366.0 [M+H]+

EXAMPLE 2

4-[5-(2-Fluoro-phenoxy)-oxazolo[5,4-d]pyrimidin-2-yl]-2,6-dimethyl-phenol

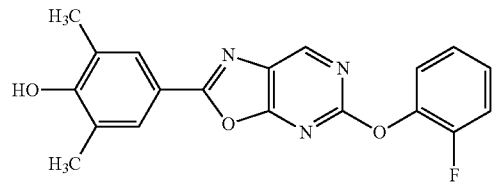 [SMILES: Cc1cc(-c2nc3cnc(Oc4ccccc4F)nc3o2)cc(C)c1O]

A solution of 510 mg of 5-(2-fluoro-phenoxy)-2-(4-methoxy-3,5-dimethyl-phenyl)-oxazolo[5,4-d]pyrimidine in 20 ml of dichloromethane was cooled to 0° C. Over a period of 10 min, 4.2 ml of a 1 M solution of boron tribromide in dichloromethane was added. The mixture was stirred at 0° C. for 1 h, and then another 2 ml of a 1 M solution of boron tribromide in dichloromethane were added. After stirring for another 1 h, 10 ml of a saturated aqueous solution of sodium hydrogencarbonate were added slowly. The aqueous layer was extracted twice with 15 ml of dichloromethane, and the combined organic layers were dried over sodium sulfate, filtered. The solvents were removed in vacuo to give 445 mg of the title compound as a white solid. LC/MS (method LC2): Rt=3.62 min; m/z=352.13 [M+H]+

Analogously to the preparation of the example compounds described above, the example compounds of the formula I listed in Table 1 were prepared. In part, they were obtained in the form of their trifluoroacetic acid salt.

TABLE 1

Example compounds of the formula I

| Example | Name | LC/MS | m/z [M + H]+ | Rt [min] |
|---|---|---|---|---|
| 3 | 5-(2-fluoro-phenoxy)-2-(3-methoxy-phenyl)-oxazolo[5,4-d]pyrimidine | LC1 | 338.2 | 1.29 |
| 4 | 4-[5-(2-fluoro-phenoxy)-oxazolo[5,4-d]pyrimidin-2-yl]-phenol | LC1 | 324.21 | 1.23 |
| 5 | 5-(2-fluoro-phenoxy)-2-(4-methoxy-3-methyl-phenyl)-oxazolo[5,4-d]pyrimidine | LC1 | 352.22 | 1.27 |
| 6 | 5-(2-fluoro-phenoxy)-2-(4-methoxy-3-trifluoromethyl-phenyl)-oxazolo[5,4-d]pyrimidine | LC1 | 406.16 | 1.38 |

TABLE 1-continued

Example compounds of the formula I

| Example | Name | LC/MS | m/z [M + H]+ | Rt [min] |
|---|---|---|---|---|
| 7 | 4-[5-(2-fluoro-phenoxy)-oxazolo[5,4-d]pyrimidin-2-yl]-2-methyl-phenol | LC1 | 338.15 | 1.28 |
| 8 | 2-(4-methoxy-3,5-dimethyl-phenyl)-5-phenoxy-oxazolo[5,4-d]pyrimidine | LC3 | 348.03 | 3.55 |
| 9 | 2-(4-methoxy-3,5-dimethyl-phenyl)-5-(pyridin-3-yloxy)-oxazolo[5,4-d]pyrimidine | LC3 | 349.01 | 2.78 |
| 10 | 4-[5-(2-fluoro-phenoxy)-oxazolo[5,4-d]pyrimidin-2-yl]-2-trifluoromethyl-phenol | LC1 | 392.11 | 1.31 |
| 11 | 2,6-dimethyl-4-[5-(pyridin-3-yloxy)-oxazolo[5,4-d]pyrimidin-2-yl]-phenol | LC1 | 335.14 | 1.15 |
| 12 | 4-[5-(3-fluorophenoxy)-oxazolo[5,4-d]pyrimidin-2-yl]-2-isopropyl-6-methyl-phenol | LC1 | 380.15 | 1.38 |
| 13 | 5-(2-fluorophenoxy)-2-(4-methanesulfonyl-3-methylphenyl)-oxazolo[5,4-d]pyrimidine | LC1 | 400.1 | 1.27 |
| 14 | 5-(2-fluorophenoxy)-2-(4-methanesulfonyl-2-methylphenyl)-oxazolo[5,4-d]pyrimidine | LC1 | 400.12 | 1.26 |

Determination of the Pharmacological Activity

A) GTP-γ-S assay using human Edg-1 receptors

In order to determine the Edg-1 receptor activation by the compounds of the invention, a GTP-γ-S (guanosine 5'-[thio]triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell line generation The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) termed as pcDNA5-FRT-TO_nFLAG_DEST-EDG-1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway conversion system, Invitrogen, cat. no. 11828-029). In addition a FLAG tag epitope was added before the 5' att recombination site to allow recombinant expression of N-terminally FLAG-tagged proteins.

For the transfection of one well, 1.08 µg of pOG44 and 0.12 µg of pcDNA5-FRT-TO_nFLAG_DEST-EDG-1 were mixed to 100 µl of serum-free Ham F-12 medium containing 6 µl of FuGENE® 6 transfection reagent. After 20 min of incubation, the transfection reagent/DNA complex was distributed dropwise on the cells. The cells were incubated for 24 h at 37° C. Then the cells from 3 wells were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 µg/ml of hygromycin B (Invitrogen, cat. no. 10687-010)). The medium was exchanged every 2 to 3 days until a resistant population of cells had grown. Cells were several times splitted and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. Cells were resuspended in a mixture of 90% of FCS and 10% of dimethylsulfoxide and stored frozen in liquid nitrogen.

(b) Membrane Preparation

A membrane preparation was obtained by standard methods from the afore-described CHO Flp-ln cell line constitutively overexpressing the human Edg-1 receptor. Briefly, the cryopreserved cells were taken in culture and grown until confluency in T175 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. No. 8418) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at −80° C. Protein concentration of the membrane preparation was determined in a sample by means of a commercial protein assay (Bio-Rad, DC Protein Assay, cat. nos. 500-0113, 500-0114, 500-0115).

(c) GTP-γ-S Assay

The Edg-1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabeled GTP-γ-S to the receptor-containing membrane, which is bound to scintillation beads, stimulates the emission of light and allows to quantify the in vitro activity of the Edg-1 agonistic compound. The assay was performed on a 96-well plate substantially according to the manufacturer's instructions. Before start of the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

Wells were charged with 10 µl of the specified assay buffer, 10 µl of a 100 µM guanosine diphosphate (GDP) solution, and 10 µl of a solution of the test compound in assay buffer/dimethylsulfoxide resulting in a final concentration of the test compound of 10 µM. For the high controls, 10 µl of a solution of sphingosine-1-phosphate (S1P; Sigma, cat. no. S-9666), resulting in a final S1P concentration of 10 µM, and for the low controls 10 µl of assay buffer, was added into respective wells instead of the solution of the test compound. All wells contained equivalent amounts of dimethylsulfoxide. Then 10 µl of a [$^{35}$S]GTP-γ-S solution (4 nM) and the Edg-1 membrane preparation obtained in (b) (15 µg membrane proteins in 100 µl of assay buffer) was added to each well. After incubation of the plates at room temperature for 5 min, 50 µl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (Micro-Beta, Wallac) over 1 min. Values were background-corrected by subtraction of the respective low control. All measurements were made in triplicate. The receptor activation by the test compound is expressed in percent of the respective high control (10 µM S1P; regarded as 100% activation). In Table 2 activations observed with example compounds at 10 µM are listed.

TABLE 2

Edg-1 receptor activation by example compounds at 10 µM in percent of the activation by 10 µM S1P

| Example | % Activation |
|---------|--------------|
| 1 | 102 |
| 2 | 115 |
| 3 | 95 |
| 4 | 83 |
| 5 | 42 |
| 6 | 87 |
| 7 | 115 |
| 8 | 94 |
| 9 | 87 |
| 10 | 107 |
| 11 | 103 |
| 12 | 112 |

TABLE 2-continued

Edg-1 receptor activation by example compounds at 10 µM in percent of the activation by 10 µM S1P

| Example | % Activation |
|---------|--------------|
| 13 | 120 |
| 14 | 69 |

It can be seen from the measurement data that the compounds are highly suitable for wound healing and in particular for treating wound healing disorders of patients with diabetes.

The invention claimed is:

1. A compound of the formula I, in any of its stereoisomeric forms, or a mixture of stereoisomeric forms in any ratio, or a physiologically acceptable salt thereof,

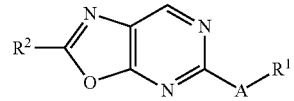

I wherein

A is chosen from NH, O or S;

$R^1$ is chosen from $C_3$-$C_7$-cycloalkyl-$C_uH_{2u}$— or Het-$C_vH_{2v}$—, wherein u and v are chosen from 1 or 2, or $R^1$ is a residue of a saturated or unsaturated, 3-membered to 10-membered, monocyclic or bicyclic ring which comprises 0, 1, 2, 3 or 4 identical or different ring heteroatoms chosen from N, O or S, wherein one or two of the ring nitrogen atoms may carry a hydrogen atom or a ($C_1$-$C_4$)-alkyl substituent and one or two of the ring sulfur atoms may carry one or two oxo groups, and wherein the residue of a ring is optionally substituted on one or more ring carbon atoms by identical or different substituents $R^{11}$;

$R^2$ is chosen from phenyl or pyridinyl, wherein the ring nitrogen atom of the pyridinyl may carry an oxy substituent, and wherein the phenyl and the pyridinyl are optionally substituted on one or more ring carbon atoms by identical or different substituents $R^{22}$ $R^{11}$ is chosen from halogen, ($C_1$-$C_4$)-alkyl, ($C_3$-$C_7$)-cycloalkyl, hydroxy, ($C_1$-$C_4$)-alkyloxy, oxo, ($C_1$-$C_4$)-alkyl-S(O)$_m$—, amino, ($C_1$-$C_4$)-alkylamino, di(($C_1$-$C_4$)-alkyl)amino, ($C_1$-$C_4$)-alkylcarbonylamino, ($C_1$-$C_4$)-alkylsulfonylamino, nitro, cyano, ($C_1$-$C_4$)-alkylcarbonyl, aminosulfonyl, ($C_1$-$C_4$)-alkylaminosulfonyl or di(($C_1$-$C_4$)-alkyl)aminosulfonyl;

$R^{22}$ is chosen from halogen, hydroxy, ($C_1$-$C_4$)-alkyl-, ($C_1$-$C_4$)-alkyloxy, ($C_1$-$C_4$)-alkyl-S(O)$_m$—, amino, nitro, cyano, hydroxycarbonyl, ($C_1$-$C_4$)-alkyloxycarbonyl, aminocarbonyl, aminosulfonyl, $R^{23}$ or $R^{23}$—O—;

$R^{23}$ is a residue of a saturated 3-membered to 7-membered, monocyclic or bicyclic ring which comprises 0, 1, 2, 3 or 4 identical or different ring heteroatoms chosen from N, O or S, wherein one or two of the ring nitrogen atoms may carry a hydrogen atom or a ($C_1$-$C_4$)-alkyl substituent and one of the ring sulfur atoms may carry one or two oxo groups, and wherein the residue of a ring is optionally substituted on one or more ring carbon atoms by identical or different substituents $R^{24}$;

$R^{24}$ is chosen from halogen, ($C_1$-$C_4$)-alkyl, hydroxy or oxo;

Het is a residue of a saturated, 4-membered to 7-membered, monocyclic heterocycle which comprises 1 or 2 identical or different ring heteroatoms chosen from N, O or S and which is bonded via a ring carbon atom, wherein the residue of a heterocycle is optionally substituted by one or more identical or different substituents chosen from fluorine or $(C_1\text{-}C_4)$-alkyl; and m is chosen from 0, 1 or 2, wherein all numbers m are independent of each other;

wherein all cycloalkyl groups, independently of each other and independently of any other substituents, are optionally substituted by one or more identical or different substituents chosen from fluorine or $(C_1\text{-}C_4)$-alkyl;

wherein all alkyl, $C_uH_{2u}$, $C_vH_{2v}$, alkenyl and alkynyl groups, independently of each other and independently of any other substituents, are optionally substituted by one or more fluorine substituents.

2. A compound of the formula I, in any of its stereoisomeric forms, or a mixture of stereoisomeric forms in any ratio, or a physiologically acceptable salt thereof, as claimed in claim 1, wherein A is chosen from O or S.

3. A compound of the formula I, in any of its stereoisomeric forms, or a mixture of stereoisomeric forms in any ratio, or a physiologically acceptable salt thereof, as claimed in claim 1, wherein $R^2$ is chosen from phenyl or pyridinyl, wherein the ring nitrogen atom of the pyridinyl may carry an oxy substituent, and wherein the phenyl and the pyridinyl are optionally substituted on one or more ring carbon atoms by identical or different substituents $R^{22}$.

4. A compound of the formula I, in any of its stereoisomeric forms, or a mixture of stereoisomeric forms in any ratio, or a physiologically acceptable salt thereof, as claimed in claim 1, wherein A is chosen from O or S;

$R^1$ is chosen from $(C_3\text{-}C_7)$-cycloalkyl-$C_uH_{2u}$— or Het-$C_vH_{2v}$—, wherein u and v are chosen from 1 or 2, or $R^1$ is a residue of a saturated or unsaturated, 3-membered to 10-membered, monocyclic or bicyclic ring which comprises 0, 1, 2, 3 or 4 identical or different ring heteroatoms chosen from N, O or S, wherein one or two of the ring nitrogen atoms may carry a hydrogen atom or a $(C_1\text{-}C_4)$-alkyl substituent and one or two of the ring sulfur atoms may carry one or two oxo groups, and wherein the residue of a ring is optionally substituted on one or more ring carbon atoms by identical or different substituents $R^{11}$; and $R^2$ is chosen from phenyl and pyridinyl, wherein the ring nitrogen atom of the pyridinyl can carry an oxy substituent, and wherein the phenyl and the pyridinyl are optionally substituted on one or more ring carbon atoms by identical or different substituents $R^{22}$.

5. A compound of the formula I, in any of its stereoisomeric forms, or a mixture of stereoisomeric forms in any ratio, or a physiologically acceptable salt thereof, as claimed in claim 1, wherein A is O.

6. A compound of the formula I, in any of its stereoisomeric forms, or a mixture of stereoisomeric forms in any ratio, or a physiologically acceptable salt thereof, as claimed in claim 1, wherein A is O;

$R^1$ is chosen from $(C_3\text{-}C_7)$-cycloalkyl-$C_uH_{2u}$— or Het-$C_vH_{2v}$—, wherein u and v are chosen from 1 and 2, or $R^1$ is a residue of a saturated or unsaturated, 3-membered to 7-membered, monocyclic ring which comprises 0, 1 or 2 identical or different ring heteroatoms chosen from N, O or S, wherein one or two of the ring nitrogen atoms may carry a hydrogen atom or a $(C_1\text{-}C_4)$-alkyl substituent and one or two of the ring sulfur atoms may carry one or two oxo groups, and wherein the residue of a ring is optionally substituted on one or more ring carbon atoms by identical or different substituents $R^{11}$;

$R^2$ is chosen from phenyl or pyridinyl, wherein the ring nitrogen atom of the pyridinyl may carry an oxy substituent, and wherein the phenyl and the pyridinyl are optionally substituted on one or more ring carbon atoms by identical or different substituents $R^{22}$;

$R^{11}$ is chosen from halogen, $(C_1\text{-}C_4)$-alkyl, $(C_1\text{-}C_4)$-alkyloxy or cyano;

$R^{22}$ is chosen from halogen, hydroxy, $(C_1\text{-}C_4)$-alkyl-, $(C_1\text{-}C_4)$-alkyloxy, cyano, $R^{23}$ or $R^{23}$—O—;

$R^{23}$ is a residue of a saturated 3-membered to 6-membered, monocyclic ring which comprises 0 or 1 ring heteroatom chosen from N, O or S, wherein one or two of the ring nitrogen atoms may carry a hydrogen atom or a $(C_1\text{-}C_4)$-alkyl substituent and one of the ring sulfur atoms may carry one or two oxo groups, and wherein the residue of a ring is optionally substituted on one or more ring carbon atoms by identical or different substituents $R^{24}$;

$R^{24}$ is chosen from fluorine, $(C_1\text{-}C_4)$-alkyl or hydroxy; and

Het is a residue of a saturated, 4-membered to 7-membered, monocyclic heterocycle which comprises 1 ring heteroatom chosen from N, O or S and which is bonded via a ring carbon atom, wherein the residue of a heterocycle is optionally substituted by one or more identical or different substituents chosen from fluorine or $(C_1\text{-}C_4)$-alkyl;

wherein all cycloalkyl groups, independently of each other and independently of any other substituents, are optionally substituted by one or more identical or different substituents chosen from fluorine or $(C_1\text{-}C_4)$-alkyl;

wherein all alkyl, $C_uH_{2u}$ and $C_vH_{2v}$ groups, independently of each other and independently of any other substituents, are optionally substituted by one or more fluorine substituents.

7. A compound of the formula I, in any of its stereoisomeric forms, or a mixture of stereoisomeric forms in any ratio, or a physiologically acceptable salt thereof, as claimed in claim 1, wherein A is O;

$R^1$ is a residue of a saturated or unsaturated, 3-membered to 7-membered, monocyclic ring which comprises 0 or 1 ring heteroatom chosen from N, O or S, wherein a ring nitrogen atom may carry a hydrogen atom or a $(C_1\text{-}C_4)$-alkyl substituent and a ring sulfur atom may carry one or two oxo groups, and wherein the residue of a ring is optionally substituted on one or more ring carbon atoms by identical or different substituents $R^{11}$;

$R^2$ is chosen from phenyl or pyridinyl, wherein the ring nitrogen atom of the pyridinyl may carry an oxy substituent, and wherein the phenyl and the pyridinyl are optionally substituted on one or more ring carbon atoms by identical or different substituents $R^{22}$;

$R^{11}$ is chosen from halogen, $(C_1\text{-}C_4)$-alkyl or $(C_1\text{-}C_4)$-alkyloxy;

$R^{22}$ is chosen from halogen, hydroxy, $(C_1\text{-}C_4)$-alkyl-, $(C_1\text{-}C_4)$-alkyloxy, $R^{23}$ or $R^{23}$—O—;

$R^{23}$ is a residue of a saturated 3-membered to 6-membered, monocyclic ring which comprises 0 or 1 ring heteroatom chosen from N, O or S, wherein one or two of the ring nitrogen atoms may carry a hydrogen atom or a $(C_1\text{-}C_4)$-alkyl substituent and one of the ring sulfur atoms may carry one or two oxo groups, and wherein the residue of a ring is optionally substituted on one or more ring carbon atoms by identical or different substituents $R^{24}$; and $R^{24}$ is chosen from fluorine, $(C_1\text{-}C_4)$-alkyl or hydroxy;

wherein all cycloalkyl groups, independently of each other and independently of any other substituents, are optionally substituted by one or more identical or different substituents chosen from fluorine or $(C_1-C_4)$-alkyl;

wherein all alkyl groups, independently of each other and independently of any other substituents, are optionally substituted by one or more fluorine substituents.

8. A compound of the formula I, in any of its stereoisomeric forms, or a mixture of stereoisomeric forms in any ratio, or a physiologically acceptable salt thereof, as claimed in claim 1, wherein A is O.

9. A compound of the formula I, or a physiologically acceptable salt thereof, as claimed in claim 1, chosen from
5-(2-fluoro-phenoxy)-2-(4-methoxy-3,5-dimethyl-phenyl)-oxazolo[5,4-d]pyrimidine,
4-[5-(2-fluoro-phenoxy)-oxazolo[5,4-d]pyrimidin-2-yl]-2,6-dimethyl-phenol,
5-(2-fluoro-phenoxy)-2-(3-methoxy-phenyl)-oxazolo[5,4-d]pyrimidine,
4-[5-(2-fluoro-phenoxy)-oxazolo[5,4-d]pyrimidin-2-yl]-phenol,
5-(2-fluoro-phenoxy)-2-(4-methoxy-3-methyl-phenyl)-oxazolo[5,4-d]pyrimidine,
5-(2-fluoro-phenoxy)-2-(4-methoxy-3-trifluoromethyl-phenyl)-oxazolo[5,4-d]pyrimidine,
4-[5-(2-fluoro-phenoxy)-oxazolo[5,4-d]pyrimidin-2-yl]-2-methyl-phenol,
2-(4-methoxy-3,5-dimethyl-phenyl)-5-phenoxy-oxazolo[5,4-d]pyrimidine,
2-(4-methoxy-3,5-dimethyl-phenyl)-5-(pyridin-3-yloxy)-oxazolo[5,4-d]pyrimidine, or
4-[5-(2-fluoro-phenoxy)-oxazolo[5,4-d]pyrimidin-2-yl]-2-trifluoromethyl-phenol.

10. A compound of the formula I, or a physiologically acceptable salt thereof, as claimed in claim 1, chosen from
2,6-dimethyl-4-[5-(pyridin-3-yloxy)-oxazolo[5,4-d]pyrimidin-2-yl]-phenol,
4-[5-(3-fluorophenoxy)-oxazolo[5,4-d]pyrimidin-2-yl]-2-isopropyl-6-methyl-phenol,
5-(2-fluorophenoxy)-2-(4-methanesulfonyl-3-methylphenyl)-oxazolo[5,4-d]pyrimidine, or
5-(2-fluorophenoxy)-2-(4-methanesulfonyl-2-methylphenyl)-oxazolo[5,4-d]pyrimidine.

11. A pharmaceutical composition, comprising at least one compound of the formula I as claimed in claim 1 or a physiologically acceptable salt thereof, and a pharmaceutically acceptable carrier.

12. A process for the preparation of a compound of the formula I as claimed in claim 1, comprising reacting a compound of the formula II with a compound of the formula III,

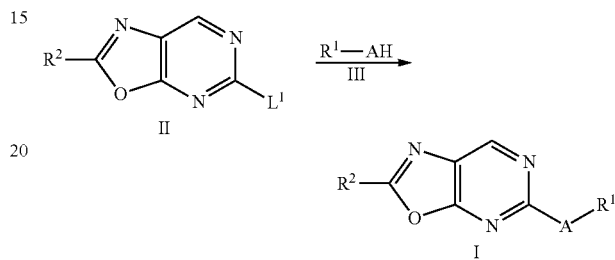

wherein the groups A, $R^1$ and $R^2$ in the compounds of the formulae II and III are defined as in the compounds of the formula I and additionally functional groups can be present in protected form or in the form of a precursor group, and the group $L^1$ is a halogen atom or a group of the formula —S(O)-Alk or —S(O)$_2$-Alk wherein Alk is $(C_1-C_4)$-alkyl.

13. A method of treating diabetic foot syndrome in a patient in need thereof comprising administering to said patient a therapeutically effective amount of the pharmaceutical composition of claim 11.

* * * * *